United States Patent [19]

Cramp et al.

[11] Patent Number: 4,618,366
[45] Date of Patent: Oct. 21, 1986

[54] CERTAIN N-(2,4-DIFLUOROPHENYL)-2-(3-TRI-FLUOROMETHYLPHENOXY)-NICOTINA-MIDES HAVING HERBICIDAL ACTIVITY

[75] Inventors: Michael C. Cramp, Romford; James Gilmour, Barkingside; Edgar W. Parnell, Hornchurch, all of England

[73] Assignee: May & Baker Limited, Dagenham, England

[21] Appl. No.: 621,102

[22] Filed: Jun. 15, 1984

Related U.S. Application Data

[63] Continuation of Ser. No. 378,224, May 14, 1982, abandoned.

[51] Int. Cl.[4] .................. C07D 213/64; C07D 213/65; A01N 43/40
[52] U.S. Cl. .......................................... 71/94; 546/291
[58] Field of Search ............................. 546/291; 71/94

[56] References Cited

U.S. PATENT DOCUMENTS 4,270,946 6/1981 Gutman ................................... 71/94
4,327,218 4/1982 Gutman ................................. 546/291

OTHER PUBLICATIONS

Cramp et al, Chemical Abstracts, vol. 97(17), Abst. No. 144, 785k, Oct. 25, 1985.

*Primary Examiner*—Alan L. Rotman
*Attorney, Agent, or Firm*—Burns, Doane, Swecker & Mathis

[57] ABSTRACT

New nicotinamide derivatives of the general formula:

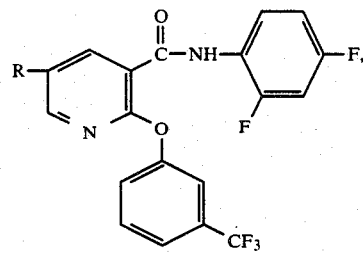

wherein R represents a hydrogen atom or a methyl group, have been found to possess useful herbicidal properties. Herbicidal compositions containing such nicotinamide derivatives are described and also processes for preparing such nicotinamide derivatives.

21 Claims, No Drawings

CERTAIN N-(2,4-DIFLUOROPHENYL)-2-(3-TRIFLUOROMETHYLPHENOXY)-NICOTINAMIDES HAVING HERBICIDAL ACTIVITY

This application is a continuation, of application Ser. No. 378,224, filed May 14, 1982 now abandoned.

DESCRIPTION

This invention relates to new nicotinamide derivatives, to processes for their preparation, to compositions containing them and to their use in agriculture as pre- and post-emergence herbicides.

In U.S. Pat. No. 4,270,946, patented on June 2, 1981 on Application No. 80,971 filed on Oct. 1, 1979 in the name of Arnold D. Gutman and assigned to Stauffer Chemical Company, there are described new compounds having the formula:-

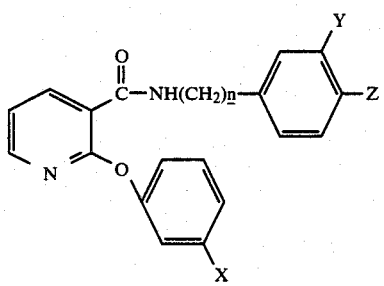

in whih n is 0 or 1; X is halogen, $C_1$–$C_3$ alkyl, trifluoromethyl or carboethoxy; Y and Z are independently hydrogen, lower alkyl, halo-lower alkyl, thio(halo-lower alkyl), lower alkoxy, nitro, cyano or halogen, provided that:

if X is carboethoxy, Z is halogen and Y is hydrogen or halogen; and if Y and Z are both halogen, X is halogen, trifluoromethyl or carboethoxy.

These compounds are stated to show various activities as pre-emergence and/or post-emergence herbicides, in some cases showing particular activity against various weed species, and, in addition, many compounds having been found to show selective herbicidal activity controlling certain weeds in certain crops, particularly wheat. The compounds in which X is halogen (particularly chloro) or trifluoromethyl and either Y or Z (or both) are hydrogen are stated to have been found, in general, to appear to be the most active overall as herbicides. Test results given in U.S. Pat. No. 4,270,946 show that none of the compounds of formula A above which were tested produced adverse effects on wheat at levels up to 2 lb/acre by pre-emergence application. Test results given in U.S. Pat. No. 4,270,946 of tests for pre-emergence activity against weeds [hairy crabgrass (*Digitaria sanguinalis*), green foxtail (*Setaria viridis*), watergrass (*Echinochloa crusgalli*), red oat (*Avena sativa*), redroot pigweed (*Amaranthus retroflexus*), Indian mustard (*Brassica juncea*) and curly dock (*Rumex crispus*)] show the compound N-phenyl-2-(3-trifluoromethylphenoxy)nicotinamide, identified in U.S. Pat. No. 4,270,946 as 'Compound No 15' and hereinafter identified for convenience in the present specification as 'Compound No 15', to be the most active of the compounds tested. Compound No 15 was shown to be well tolerated by pre-emergence application to wheat but less well tolerated by soyabeans, rice, cotton, corn and milo. It may be deduced from the test results on weeds and crops given in U.S. Pat. No. 4,270,946 that Compound No 15 is the most interesting of the compounds specifically disclosed in U.S. Pat. No. 4,270,946 for the control of weeds by pre-emergence application in wheat.

As a result of research and experimentation, it has been found that the new nicotinamide derivatives of the general formula:

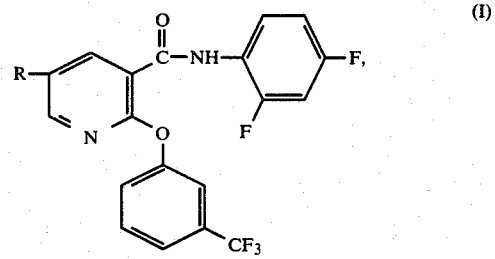

wherein R represents a hydrogen atom or a methyl group, are surprisingly superior as herbicides which may be used selectively for the control of the growth of weeds by pre-emergence application in crops, in comparison with the generality of the compounds of formula A disclosed in U.S. Pat. No. 4,270,946 and more especially Compound No. 15. The compounds of general formula I, wherein R is as hereinbefore defined, may also be used selectively for the control of weeds by post-emergence application in crops and for the control of weeds in non-crop growing areas by pre- or post-emergence application.

The compound of general formula I wherein R represents a hydrogen atom [i.e. N-(2,4-difluorophenyl)-2-(3-trifluoromethylphenoxy)nicotinamide] is, according to the present invention, preferred, more especially for the selective control of the growth of weeds by pre-emergence application in crops of soyabean, cotton, maize, wheat and sunflower before emergence of the crops.

The compound of general formula I wherein R represents a methyl group [i.e. N-(2,4-difluorophenyl)-5-methyl-2-(3-trifluoromethylphenoxy)nicotinamide] is particularly useful for the selective control of the growth of weeds by pre-emergence application in crops of soyabean, cotton, maize and wheat before emergence of the crops.

The surprising superiority of the compounds of general formula I, wherein R is as hereinbefore defined, over Compound No 15 as herbicides for the selective control of the growth of weeds by pre-emergence application in crops, more especially soyabean, cotton, maize, wheat and sunflower, is demonstrated in the following experiment, wherein the compound of general formula I wherein R represents a hydrogen atom [i.e. N-(2,4-difluorophenyl)-2-(3-trifluoromethylphenoxy)nicotinamide] is identified as 'Compound A', the compound of general formula I wherein R represents a methyl group [i.e. N-(2,4-difluorophenyl)-5-methyl-2-(3-trifluoromethylphenoxy)nicotinamide] is identified as 'Compound B' and 'Compound No 15' is as hereinbefore identified. (An alternative name for Compound B is 2-(3-trifluoromethylphenoxy)-N-(2,4-difluorophenyl)-5-methylnicotinamide).

Weed Control and Crop Tolerance Test

Appropriate quantities of the test compounds were dissolved in acetone to give solutions equivalent to application rates of 0.031, 0.063, 0.125, 0.25, 0.5, 1.0 and 2.0 kg of test compound per hectare. These solutions were applied from a standard laboratory herbicide sprayer using a flat fan jet travelling at 1.6 m.p.h. (2.6 km/hour) and delivering the equivalent of 260 liters of spray fluid per hectare.

The following combinations of crop and weed seeds were sown on the surface of unsterilized loam in 100 mm-square plastic plant pots and then covered with similar soil:

1. Soyabean (3 seeds per pot) and *Digitaria sanguinalis* (20 seeds per pot).
2. Cotton (3 seeds per pot) and *Ipomoea purpurea* (15 seeds per pot).
3. Maize (3 seeds per pot) and *Echinochloa crus-galli* (25 seeds per pot).
4. Wheat (7 seeds per pot) and *Abutilon theophrasti* (20 seeds per pot).
5. Sunflower (3 seeds per pot) and *Avena fatua* (10 seeds per pot).

The test compounds were applied to the soil surface at the application rates and by the procedure indicated above. Three pots of each crop/weed combination was allocated to each treatment, with unsprayed controls and controls sprayed with acetone alone. After treatment, the pots were kept in the greenhouse and were watered overhead. Twenty days after spraying, the percentage bulk reduction (numbers and height) of plant growth in the pots which had been sprayed with the test compounds was determined by visual comparison with the plant growth in the unsprayed controls and the controls sprayed with acetone alone. The mean percentage reduction in plant growth was calculated for each test compound treatment and the application rate of each compound which gave a 20% inhibition of the growth (ED20) of each crop plant and a 90% inhibition of growth (ED90) of each weed species was determined. Where the effective dose (ED) lay between two rates of application, a dose range was recorded.

The results obtained are presented below in the following Table I, in which species are identified by the following abbreviations:

Ds=*Digitaria sanguinalis*
Ip=*Ipomoea purpurea*
Ec=*Echinochloa crus-galli*
At=*Abutilon theophrasti*
Af=*Avena fatua*

TABLE I

| | TEST COMPOUND | | |
|---|---|---|---|
| | Compound A | Compound B | Compound No 15 |
| Crop tolerance (ED20) | | | |
| Soyabean | 1.0 | 0.5 | 0.5 |
| Cotton | 0.25 | 0.125 | 1.0 |
| Maize | 0.5 | 0.125–0.25 | 0.5–1.0 |
| Wheat | 1.0 | 0.25–0.5 | >2.0 |
| Sunflower | >>2.0 | 0.031 | 0.5–1.0 |
| Weed control (ED90) | | | |
| Ds | 0.031 | <0.031 | 0.125 |
| Ip | 2.0 | 1.0–2.0 | >2.0 |
| Ec | 0.125 | 0.063 | 0.5 |
| At | 0.25 | 0.063 | 0.5 |
| Af | 0.5–1.0 | 0.125–0.25 | >2.0 |

The following symbols which appear in the above Table I have the following meanings:

'>>' means 'much greater than '
'>' means 'greater than '
'<' means 'less than'

The above experimental results show that, by pre-emergence application, Compound A and Compound B are 4 and more than 4 times, respectively, as active as Compound No 15 in controlling the growth of *Digitaria sanguinalis* (hairy crabgrass), 4 and 8 times, respectively, as active as Compound No 15 in controlling the growth of *Echinochloa crus-galli* (watergrass or barnyard grass), and *Avena fatua* (wild oat), 2 and 8 times, respectively, as active as Compound No 15 in controlling the growth of *Abutilon theophrasti* (velvet leaf) and that each is up to twice as active as Compound No 15 in controlling the growth of *Ipomoea purpurea* (morning glory).

Although Compounds A and B exhibit greatly enhanced herbicidal activity against weeds, particularly the grass weeds, by pre-emergence application in comparison with Compound No 15, they also exhibit a selectivity (as reflected in the ratio of crop tolerance ED20 to weed conrol ED90 results) in controlling the growth of weeds without causing unacceptable adverse effects on the growth of crops when applied before emergence of the crops, which is at least as good as, and frequently much superior to, that exhibited by Compound No 15. For example, when the test compounds were applied before the emergence of maize, this crop tolerated 4 times the application rate of Compound A and 2 and 4 times the application rate of Compound B, respectively, required to control the growth of the important grass weed *Echinochloa crus-galli* by pre-emergence application, whereas in comparison maize tolerated only 1–2 times the application rate of Compound No 15 required to control this weed. Similarly, both Compound A and Compound B exhibited greater selectivity than Compound No 15 in respect of controlling the growth of *Digitaria sanguinalis* and *Abutilon theophrasti* and their tolerance by maize by pre-emergence application before emergence of the crop. The selectivity of Compound No 15, as reflected by the ratio of the application rate tolerated by soyabean (ED20) by application before emergence of the crop and the application rates required to control the growth of *Digitaria sanguinalis, Echinochloa crus-galli* and *Abutilon theophrasti* by pre-emergence application is very narrow, whereas the comparable selectivity of Compound A and Compound B in respect of that crop and weeds is very much wider. Thus, the growth of all three of these weeds were controlled at a pre-emergence application rate of Compound B of 0.063 kg/ha (ED90), while soyabean tolerated (ED20) 8 times that rate of application when applied before emergence of the crop and the growth of all three of these weeds were controlled at a pre-emergence application rate of Compound A of 0.25 kg/ha (ED90), while soyabean tolerated (ED20) 4 times that rate of application when applied before the emergence of the crop, whereas the pre-emergence rate of application of Compound No 15 of 0.5 kg/ha (ED90) required to control the growth of these three weeds was the same as the rate of application of Compound No 15 tolerated by soyabean (ED20) when applied before the emergence of the crop. Compound No 15 is well tolerated by wheat when applied before the emergence but has low pre-emergence herbicidal activity against the very important grass weed species *Avena fatua* whereas pre-emergence rates of application (ED90) of both Compound B and, more especially, Compound A required to control the growth of *Avena fatua* was significantly lower than the rate of application (ED20) tolerated by wheat when applied before emergence of the crop. Compound A was particularly well tolerated by sunflower when applied before the emergence of the crop at a rate of application (ED20) substantially higher than the rates of pre-emergence application required to control the growth of the five tested weed species (ED90), including the important weed species *Ipomoea purpurea*, whereas Compound No 15 did not control the growth of *Ipomoea purpurea* at a rate of pre-emergence application (ED90 2.0 kg/ha) in excess of the rate of application tolerated by sunflower (ED20 0.5-1.0 kg/ha) when applied before the emergence of the crop. Compound B is not well tolerated by sunflower when applied before the emergence of that crop and would not generally be suitable for controlling the growth of weeds in that crop by pre-emergence application.

In other experiments on herbicidal activity carried out on Compound A, Compound B and Compound No 15, the following results have been obtained:

TEST METHOD

Weed Control Test

(a) General

Appropriate quantities of the test compounds were dissolved in acetone to give solutions equivalent to application rates of 0.5, 1, 2 or 4 kg of test compound per hectare. These solutions were applied from a standard laboratory herbicide sprayer using a flat fan jet traveling at 1.6 m.p.h. (2.6 km/hour) and delivering the equivalent of 530 liters of spray fluid per hectare.

(b) Weed Control: Pre-emergence application

Weed seeds were sown on the surface of John Innes No. 1 potting compost (7 parts by volume of sterilized loam, 3 parts by volume of peat and 2 parts by volume of fine grit) in 9 cm diameter bitumenised paper pots. The quantities of seed per pot were as follows:

| Weed species | Approximate number seeds/pot |
|---|---|
| (i) Broad leafed weeds | |
| Sinapis arvensis | 30-40 |
| Polygonum lapathifolium | 30-40 |
| Stellaria media | 30-40 |
| (ii) Grass weeds | |
| Avena fatua | 15-20 |
| Alopecurus myosuroides | 30-40 |
| Echinochloa crus-galli | 20-40 |

The test compounds were applied to the uncovered seeds as described in (a) above at dose rates equivalent to 0.25, 0.5, 1, 2 or 8 kg of test compound per hectare within the dose ranges hereinafter indicated and the seeds were covered with 25 ml of sharp sand after spraying. A single pot of each weed species was allocated to each treatment, with unsprayed controls and controls sprayed with acetone alone. After treatment, the pots were kept in the greenhouse and were watered overhead. Visual assessment of weed control activity was made 19 to 28 days after spraying. The results were expressed as the minimum effective dose (MED) in kg/ha which gave 90% reduction in growth or kill of the weeds in comparison with plants in the control pots. The results obtained are presented below in Table II.

(c) Weed Control: Post-emergence application

Weed species were grown and then transplanted at the seedling stage into John Innes No. 1 potting compost in 9 cm diameter bitumenised paper pots, except for *Avena fatua*, which was sown directly in the test pot and not transplanted. The plants were then grown in the greenhouse until ready for spraying with the test compounds. The number of plants per pot and the growth of the plant at spraying were as follows:

| Weed species | Number of plants/pot | Growth stages at spraying |
|---|---|---|
| (i) Broad leafed weeds | | |
| Polygonum lapathifolium | 5 | 1-1½ pairs of leaves |
| Stellaria media | 5 | 4-6 leaves |
| Abutilon theophrasti | 3 | 2 pairs of leaves |
| (ii) Grass Weeds | | |
| Avena fatua | 10 | 1 leaf |
| Alopercurus myosuroides | 5 | 1½ leaves |
| Echinochloa crus-galli | 5 | 1-2 leaves |

The test compounds were applied to the plants as described in (1) (a) above at dose rates equivalent to 0.25, 0.5, 1, 2, 4 and 8 kg of test compound per hectare within the dose range hereinbefore indicated. A single pot of each weed species was allocated to each treatment, with unsprayed controls and controls sprayed with acetone alone. After spraying, the pots were watered overhead, commencing 24 hours after spraying. Assessment of the control of the growth of the weeds was made 19-28 days after spraying by recording the number of plants which had been killed and the reduction in growth. The results were expressed as the minimum effective dose (MED) in kg/ha which gave 90% reduction in growth or kill of the weeds in comparison with the plants in the control pots. The results obtained are presented below in Table III.

KEY TO WEED SPECIES

(a) GRASS WEEDS

Am = *Alopecurus myosuroides*
Af = *Avena fatua*
Ec = *Echinochloa crus-galli*

(b) BROAD-LEAF WEEDS

Sm = *Stellaria media*
Pl = *Polygonum lapathifolium*
Sa = *Sinapis arvensis*
At = *Abutilon theophrasti*

TABLE II

| Test Compound | PRE-EMERGENCE MED (kg/ha) | | | | | | Dose Range (kg/ha) |
|---|---|---|---|---|---|---|---|
| | Pl | Sa | Sm | Am | Af | Ec | |
| Compound A | <1 | <1 | <1 | <1 | <1 | <1 | 1-4 |
| Compound B | 0.5 | <0.5 | <0.5 | <0.5 | <0.5 | <0.5 | 0.5-4 |
| Compound No 15 | >4 | <1 | <1 | >1 | >4 | <1 | 1-4 |

TABLE III

| Test Compound | POST-EMERGENCE MED (kg/ha) | | | | | | Dose Range (kg/ha) |
| --- | --- | --- | --- | --- | --- | --- | --- |
| | At | Pl | Sm | Am | Af | Ec | |
| Compound A | <1 | 1 | <1 | >>4 | >4 | 4 | 1–4 |
| Compound B | 0.5 | >>4 | 0.5 | >4 | 2–4 | >>4 | 0.5–4 |
| Compound No 15 | <1 | <1 | 4 | NR | NR | 4 | 1–4 |

The following symbols which appear in Tables II and III have the following meanings:

'>>' means 'much greater than'
'>' means 'greater than'
'<' means 'less than'
'NR' means 'no reduction at any dose rate applied'

According to a feature of the present invention, there is provided a method for controlling the growth of weeds (i.e. undesired vegetation) at a locus which comprises applying to the locus a herbicidally effective amount of at least one nicotinamide derivative of general formula I. For this purpose, the nicotinamide derivatives are normally used in the form of herbicidal compositions (i.e. in association with compatible diluents or carriers suitable for use in herbicidal compositions), for example as hereinafter described.

The compounds of general formula I show herbicidal activity against dicotyledonous (i.e. broad-leafed) and monocotyledonous (e.g. grass) weed by pre- and/or post-emergence application.

By the term "pre-emergence application" is meant application to the soil in which the weed seeds or seedlings are present before emergence of the weeds above the surface of the soil. By the term "post-emergence application" is meant application to the aerial or exposed portions of the weeds which have emerged above the surface of the soil. For example, the compounds of general formula I may be used to control the growth of broad-leafed weeds, for example, *Aethusa cynapium, Abutilon theophrasti, Amaranthus retroflexus, Amsinckia intermedia, Anagallis arvensis, Anthemis arvensis, Atriplex patula, Brassica nigra, Capsella bursa-pastoris, Chenopodium album, Chrysanthemum segetum, Cirsium arvense, Datura stramonium, Desmodium tortuosum, Emex australis, Euphorbia helioscopia, Fumaria officinalis, Galeopis tetrahit, Galium aparine, Geranium dissectum, Ipomea purpurea, Lamium purpureum, Lapsana communis, Matricaria inodora, Monochoria vaginalis, Papaver rhoeas, Physalis longifolia, Plantago lanceolata,* Polygonum spp., (e.g. *Polygonum aviculare, Polygonum convolvulus* and *Polygonum persicaria), Portulaca oleracea, Raphanus raphanistrum, Rotala indica, Rumex obtusifolius, Saponaria vaccaria, Scandix pecten-veneris, Senecio vulgaris, Sesbania florida, Sida spinosa, Silene alba, Sinapis arvensis, Solanum nigrum, Sonchus arvensis, Spergula arvensis, Stellaria media, Thlaspi arvense, Tribulus terrestria, Urtica urens, Veronica hederifolia, Veronica persica, Viola arvensis* and *Xanthium strumarium*, and grass weeds, for example, *Alopecurus myosuroides, Apera spica-venti, Argrostis stolonifera, Avena fatua, Avena ludoviciana,* Brachiaria supp., *Bromus sterilis,* Bromus tectorum, Cenchrus spp., Cynodon dactylon, *Digitaria sanquinalis, Echinochloa crus-galli, Eleusine indica, Setaria viridis* and *Sorghum halepense.*

The amounts of compounds of general formula I applied vary with the nature of the weeds, the compositions used, the time of application, the climatic and edaphic conditions and (when used to control the growth of weeds in crop-growing areas) the nature of the crops. When applied to a crop-growing area, the rate of application should be sufficient to control the growth of weeds without causing substantial permanent damage to the crop. In general, taking these factors into account, application rates between 0.01 kg and 10 kg of active material per hectare give good results. However, it is to be understood that higher or lower application rates may be used, depending upon the particular problem of weed control encountered.

The compounds of general formula I may be used to control selectively the growth of weeds, for example to control the growth of those species hereinbefore mentioned, by pre- or post-emergence application in a directional or non-directional fashion, e.g. by directional or non-directional spraying, to a locus of weed infestation which is an area used, or to be used, for growing crops, for example cereals, e.g. wheat, barley, maize and rice, soya beans, field and dwarf beans, peas, lucerne, cotton, peanuts, and permanent or sown grassland before or after sowing of the crop or before or after emergence of the crop and, in the case of the compound of general formula I wherein R represents a hydrogen atom, to a locus of weed infestation which is an area used or to be used to grow a crop of sunflower before or after the sowing of the crop and before emergence of the crop. For the selective control of weeds at a locus of weed infestation which is an area used, or to be used, for the growing of crops, e.g. the crops hereinbefore mentioned, application rates between 0.01 kg and 4.0 kg, and preferably between 0.05 kg and 2.0 kg, of active material per hectare are particularly suitable. More particularly, the compounds of general formula I may be used to control selectively the growth of broad leafed and grass weeds, for example to control the growth of those weed species hereinbefore mentioned, by pre-emergence application, in a non-directional fashion, e.g. by non-directional spraying, to an area used for growing cereal crops, for example wheat, barley, maize or rice, soyabean, cotton and, in the case of the compound of general formula I wherein R represents a hydrogen atom, sunflower, before emergence of both the crop and weeds.

For this purpose, i.e. the selective control of broad leafed and grass weeds by pre-emergence application to an area used for growing cereal crops, soyabean, cotton and sunflower, application rates between 0.01 and 4.0 kg, and preferably between 0.05 kg and 2.0 kg, of active material per hectare are particularly suitable.

The compounds of general formula I may also be used to control the growth of weeds, especially those indicated above, by pre- or post-emergence application in established orchards and other tree-growing areas, for example forests, woods and parks, and plantations, e.g. sugar cane, oil palm and rubber plantations. For this purpose they may be applied in a directional or non-directional fashion (e.g. by directional or non-directional spraying) to the weeds or to the soil in which they are expected to appear, before or after planting of the trees or plantations at application rates between 0.25 kg and 10.0 kg, and preferably between 0.5 kg and 4.0 kg, of active material per hectare.

The compounds of general formula I may also be used to control the growth of weeds, especially those indicated above, at loci which are not crop-growing areas but in which the control of weeds is nevertheless desirable. Examples of such non-crop-growing areas include airfields, industrial sites, railways, roadside verges, the verges of rivers, irrigation and other waterways, scrublands and fallow or uncultivated land, in particular where it is desired to control the growth of weeds in order to reduce fire risks. When used for such purposes in which a total herbicidal effect is frequently desired, the active compounds are normally applied at dosage rates higher than those used in crop-growing areas as hereinbefore described. The precise dosage will depend upon the nature of the vegetation treated and the effect sought. Pre- or post-emergence application, and preferably pre-emergence application, in a directional or non-directional fashion (e.g. by directional or non-directional spraying) at application rates between 1.0 kg and 20.0 kg, and preferably between 2.0 and 10.0 kg, of active material per hectare are particularly suitable for this purpose.

When used to control the growth of weeds by pre-emergence application, the compounds of general formula I may be shallowly incorporated into the soil in which the weeds are expected to emerge. It will be appreciated that when the compounds of general formula I are used to control the growth of weeds by post-emergence application, i.e. by application to the aerial or exposed portions of emerged weeds, the compounds of general formula I will also normally come into contact with the soil and may also then exercise a pre-emergence control on later-germinating weeds in the soil.

Where especially prolonged weed control is required, the application of the compounds of general formula I may be repeated if required.

According to a further feature of the present invention, there are provided compositions suitable for herbicidal use comprising one or more of the nicotinamide derivatives of general formula I in association with, and preferably homogeneously dispersed in, one or more compatible herbicidally-acceptable diluents or carriers (i.e. diluents or carriers of the type generally accepted in the art as being suitable for use in herbicidal compositions and which are compatible with compounds of general formula I). The term "homogeneously dispersed" is used to include compositions in which the compounds of general formula I are dissolved in the other components. The term "herbicidal compositions" is used in a broad sense to include not only compositions which are ready for use as herbicides but also concentrates which must be diluted before use. Preferably, the compositions contain from 0.05 to 90% by weight of one or more compounds of general formula I.

The herbicidal compositions may contain both a diluent or carrier and a surface-active (e.g. wetting, dispersing, or emulsifying) agent. Surface-active agents which may be present in herbicidal compositions of the present invention may be of the ionic or non-ionic types, for example sulphoricinoleates, quaternary ammonium derivatives, products based on condensates of ethylene oxide with nonyl- or octylphenols, or carboxylic acid esters of anhydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphonosuccinates and alkali and alkaline earth metal salts of high molecular weight sulphonic acid derivatives such as sodium and calcium lignosulphonates.

Suitably, herbicidal compositions according to the present invention may comprise from 0.05% to 10% of surface-active agent but, if desired, herbicidal compositions according to the present invention may comprise higher proportions of surface-active agent, for example up to 15% in liquid emulsifiable suspension concentrates and up to 25% in liquid water soluble concentrates.

Examples of suitable solid diluents or carriers are aluminium silicate, talc, calcined magnesia, kieselguhr, tricalcium phosphate, powdered cork, absorbent carbon black and clays such as kaolin and bentonite. The solid compositions (which may take the form of dusts, granules or wettable powders) are preferably prepared by grinding the compounds of general formula I with solid diluents or by impregnating the solid diluents or carriers with solutions of the compounds of general formula I in volatile solvents, evaporating the solvents and, if necessary, grinding the products so as to obtain powders. Granular formulations may be prepared by absorbing the compounds of general formula I (dissolved in volatile solvents) onto the solid diluents or carriers in granular form and evaporating the solvents, or by granulating compositions in powder form obtained as described above. Solid herbicidal compositions, particularly wettable powders, my contain wetting or dispersing agent (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, acetophenone, cyclohexanone, isophorone, toluene, xylene and mineral, animal and vegetable oils (and mixtures of these diluents). Surface-active agents, which may be present in the liquid compositions, may be ionic or non-ionic (for example of the types described above) and may, when liquid, also serve as diluents or carriers.

Wettable powders and liquid compositions in the form of concentrates may be diluted with water or other suitable diluents, for example mineral or vegetable oils, particularly in the case of liquid concentrates in which the diluent or carrier is an oil, to give compositions ready for use. When desired, liquid compositions of the compound of general formula I may be used in the form of self-emulsifying concentrates containing the active substances dissolved in the emulsifying agents or in solvents containing emulsifying agents compatible with the active substances, the simple addition of water to such concentrates producing compositions ready for use.

Liquid concentrates in which the diluent or carrier is an oil may be used without further dilution using the electrostatic spray technique.

Herbicidal compositions according to the present invention may also contain, if desired, conventional adjuvants such as adhesives, protective colloids, thickeners, penetrating agents, stabilisers, sequestering agents, anti-caking agents, colouring agents and corrosion inhibitors. These adjuvants may also serve as carriers or diluents.

Preferred herbicidal compositions according to the present invention are aqueous suspension concentrates which comprise from 10 to 70% w/v of one or more compounds of general formula I, from 2 to 10% w/v of surface-active agent, from 0.1 to 5% w/v of thickener and from 15 to 87.9% by volume of water; wettable powders which comprise from 10 to 90% w/w of one or more compounds of general formula I, from 2 to 10% w/w of surface-active agent and from 10 to 88% w/w of solid diluent or carrier; liquid water soluble concentrates which comprise from 10 to 30% w/v of one or more compounds of general formula I, from 5 to 25% w/v of surface-active agent and from 45 to 85% by volume of water-miscible solvent, e.g. dimethylformamide; liquid emulsifiable suspension concentrates which comprise from 10 to 70% w/v of one or more compounds of general formula I, from 5 to 15% w/v of surface-active agent, from 0.1 to 5% w/v of thickener and from 10 to 84.9% by volume of organic solvent; granules which comprise from 2 to 10% of one or more compounds of general formula I, from 0.5 to 2% w/w of surface-active agent and from 88 to 97.5% w/w of granular carrier and emulsifiable concentrates which comprise from 0.05 to 90% w/v, and preferably from 1 to 60% w/v, of one or more compounds of general formula I, from 0.01 to 10% w/v, and preferably from 1 to 10% w/v, of surface-active agent and from 9.99 to 99.94%, and preferably from 39 to 98.99%, by volume of organic solvent.

Herbicidal compositions according to the present invention may also comprise the compounds of general formula I in association with, and preferably homogeneously dispersed in, one or more other pesticidally active compounds and, if desired, one or more compatible pesticidally acceptable diluents or carriers, surface-active agents and conventional adjuvants as hereinbefore described. Examples of other pesticidally active compounds which may be included in, or used in conjunction with, the herbicidal compositions of the present invention include herbicides, for example to increase the range of weed species controlled, for example alachlor [α-chloro-2,6-diethyl-N-(methoxymethyl)acetanilide], asulam [methyl(4-aminobenzenesulphonyl)-carbamate], alloxydim Na [sodium salt of 2-(1-allyloxyaminobutylidene)-5,5-dimethyl-4-methoxycarbonylcyclohexane-1,3-dione], atrazine [2-chloro-4-ethylamino-6-isopropylamino-1,3,5-triazine], barban [4-chlorobut-2-ynyl N-(3-chlorophenyl)carbamate], benzoylprop-ethyl [ethyl N-benzoyl-N-(3,4-dichlorophenyl-2-aminopropionate], bromoxynil [3,5-dibromo-4-hydroxybenzonitrile], butachlor [N-(butoxymethyl)-α-chloro-2,6-diethylacetanilide], butylate [S-ethyl N,N-diisobutyl(thiocarbamate)], carbetamide [D-N-ethyl-2-(phenoxycarbamoyloxy)propionamide], chlorfenpropmethyl [methyl 2-chloro-3-(4-chlorophenyl)propionate], chlorpropham [isopropyl N-(3-chlorophenyl)carbamate], chlortoluron [N'-(3-chloro-4-methylphenyl)-N,N-dimethylurea], cyanazine [2-chloro-4-(1-cyano-1-methylethylamino)-6-ethylamino-1,3,5-triazine], cycloate [N'-cyclohexyl-N-ethyl-S-ethyl(thiocarbamate)], 2,4-D[2,4-dichlorophenoxyacetic acid], dalapon (2,2-dichloropropionic acid], 2,4-DB [4-(2,4-dichlorophenoxy)butyric acid], desmedipham [3-(ethoxycarbonylamino)phenyl N-phenyl-carbamate], diallate [S-2,3-dichloroallyl-N,N-di-isopropyl(thiocarbamate)], dicamba [3,6-dichloro-2-methoxybenzoic acid], dichlorprop [(±)-2-(2,4-dichlorophenoxy)propionic acid], difenzoquat [1,2-dimethyl-3,5-diphenyl-pyrazolium salts], dimefuron {4-[2-chloro-4-(3,3-dimethylureido)phenyl]-2-t-butyl-1,3,4-oxadiazolin-5-one, dinitramine [N¹, N¹-diethyl-2,6-dinitro-4-trifluoromethyl-m-phenylenediamine], diuron [N'-(3,4-dichlorophenyl)-N,N-dimethylurea], EPTC [S-ethyl N,N-dipropyl(thiocarbamate)], ethofumesate [2-ethoxy-2,3-dihydro-3,3-dimethylbenzofuran-5-yl methylsulphonate], flampropisopropyl [isopropyl (±)-2-(N-benzoyl-3-chloro-4-fluoroanilino)-propionate], flampropmethyl [methyl (±)-2-(N-benzoyl-3-chloro-4-fluoroanilino)propionate], fluometuron [N'-(3-trifluoromethylphenyl)-N,N-dimethylurea], ioxynil [4-hydroxy-3,5-di-iodobenzonitrile], isoproturon [N'-(4-isopropylphenyl)-N,N-dimethylurea], linuron [N-(3,4-dichlorophenyl)-N-methoxy-N-methylurea], MCPA [4-chloro-2-methylphenoxyacetic acid], MCPB [4-(4-chloro-2-methylphenoxy)butyric acid], mecoprop [(±)-2-(4-chloro-2-methylphenoxy)propionic acid], metamitron [4-amino-3-methyl-6-phenyl-1,2,4-triazin-5(4H)-one], methabenzthiazuron [N-(benzothiazol-2-yl)-N,N'-dimethylurea], metribuzin [4-amino-6-t-butyl-3-(methylthio)-1,2,4-triazin-5(4H)-one], molinate [S-ethyl N,N-hexamethylene(thiocarbamate)], oxadiazon [3-(2,4-dichloro-5-isopropoxyphenyl)-5-t-butyl-1,3,4-oxadiazolin-2-one], paraquat [1,1'-dimethyl-4,4'-bipyridylium salts], pebulate [S-propyl N-butyl-N-ethyl (thiocarbamate)], phenmedipham [3-(methoxycarbonylamino)-phenyl N-(3-methylphenyl)carbamate], prometryne [4,6-bisisopropylamino-2-methylthio-1,3,5-triazine], propachlor [α-chloro-N-isopropylacetanilide], propanil [N-(3,4-dichlorophenyl)-propionamide], propham [isopropyl N-phenylcarbamate], pyrazone [5-amino-4-chloro-2-phenylpyridazin-3(2H)-one], simazine [2-chloro-4,6-bisethylamino-1,3,5-triazine], TCA (trichloroacetic acid), thiobencarb [S-(4-chlorobenzyl)-N,N-diethylthiolcarbamate], triallate [S-2,3,3-trichloroallyl N,N-di-isopropyl(thiocarbamate)], and trifluralin [2,6-dinitro-N,N-dipropyl-4-trifluoromethylaniline]; insecticides, e.g. carbaryl [naphth-1-yl N-methylcarbamate]; synthetic pyrethroids, e.g. permethrin and cypermethrin; and fungicides, e.g. 2,6-dimethyl-4-tridecyl-morpholine, methyl N-(1-butylcarbamoyl-benzimidazol-2-yl)carbamate, 1,2-bis-(3-methoxycarbonyl-2-thioureido)benzene, isopropyl 1-carbamoyl-3-(3,5-dichlorophenyl)hydantoin and 1-(4-chlorophenoxy)-3,3-dimethyl-1-(1,2,4-triazol-1-yl)-butan-2-one. Other biologically active materials which may be included in, or used in conjunction with, the herbicidal compositions of the present invention are plant growth regulators, e.g. succinamic acid, (2-chloroethyl)trimethylammonium chloride and 2-chloroethane-phosphonic acid; or fertilizers, e.g. containing nitrogen, potassium and phosphorus and trace elements known to be essential to successful plant life, e.g. iron, magnesium, zinc, manganese, cobalt and copper.

Pesticidally active compounds and other biologically active materials which may be included in, or used in conjunction with, the herbicidal compositions of the present invention, for example those hereinbefore mentioned, and which are acids, may, if desired, be utilized in the form of conventional derivatives, for example alkali metal and amine salts and esters.

The following Example illustrates herbicidal compositions according to the present invention.

EXAMPLE 1

An aqueous suspension concentrate was formed from:

| | |
|---|---|
| N—(2,4-difluorophenyl)-2-(3-trifluoromethylphenoxy)nicotinamide | 50% w/v |
| Ethylan BCP | 1.0% w/v |
| Sopropon T36 (sodium salt of polycarboxylic acid) | 0.2% w/v |

| | |
|---|---|
| Ethylene glycol | 5% w/v |
| Rhodigel 23 (polysaccharide xanthan gum thickener) | 0.15% w/v |
| distilled water to | 100% by volume | by intimately mixing the ingredients and grinding in a ball-mill for 24 hours. The concentrate thus obtained may be dispersed in water and applied at an application rate of 1.0 kg of aqueous suspension concentrate in 300 liters of spray fluid per hectare to control the growth of *Echinochloa crus-galli, Digitaria sanguinalis, Setaria viridis, Amaranthus retroflexus, Abutilon theophrasti* and *Sinapis arvensis* by pre-emergence application in a crop of wheat, soyabean, maize or sunflower before emergence of the crop.

Similar aqueous suspension concentrates may be prepared as described above by replacing the N-(2,4-difluorophenyl)-2-(3-trifluoromethylphenoxy)nicotinamide by N-(2,4-difluorophenyl)-5-methyl-2-(3-trifluoromethylphenoxy)nicotinamide.

(Ethylan BCP is a nonylphenol/ethylene oxide condensate containing 9 moles of ethylene oxide per mol of phenol).

The compounds of general formula I may be prepared by the application or adaptation of known methods for the preparation of nicotinamide derivatives.

According to a feature of the present invention, the new nicotinamide derivatives of general formula I, wherein R is as hereinbefore defined, are prepared by the process which comprises the reaction of 2,4-difluoroaniline or an acid addition salt thereof, e.g. the hydrochloride, with a compound of the general formula:

(II)

wherein Q represents a group of the general formula:

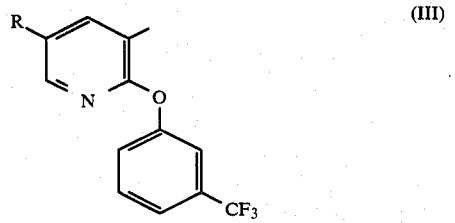
(III)

(wherein R is as hereinbefore defined) and T represents a bromine or, preferably, chlorine atom or a group of the general formula:

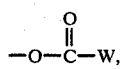
(IV)

wherein W represents a group of general formula III (wherein R is as hereinbefore defined) or a straight- or branched-chain alkyl group containing from 1 to 4 carbon atoms.

The reaction between 2,4-difluoroaniline or acid addition salts thereof, and the compounds of general formula II may be effected in the presence of a suitable inert organic solvent, for example an aromatic hydrocarbon e.g. benzene or toluene, or dimethylformamide or a halohydrocarbon, e.g. dichloromethane or tetrachloroethane, and at a temperature of from the ambient temperature to the reflux temperature of the reaction mixture and optionally in the presence of a base, for example triethylamine or potassium carbonate.

According to a further feature of the present invention, the new nicotinamide derivatives of general formula I, wherein R is as hereinbefore defined, are prepared by the process which comprises the reaction of a compound of the general formula:

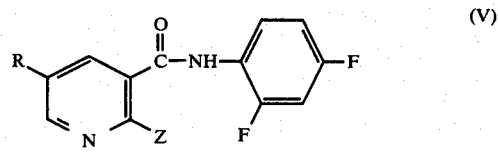
(V)

(wherein Z represents a chlorine or bromine atom and R is as hereinbefore defined) with an alkali metal, e.g. sodium or potassium, salt of 3-trifluoromethylphenol.

The reaction between the compound of general formula V and the sodium salt of 3-trifluoromethylphenol may be effected by heating the compound of general formula V with the sodium salt of 3-trifluoromethylphenol in a suitable inert organic solvent, for example diethyleneglycol dimethyl ether, or preferably, in the presence of 3-trifluoromethylphenol which serves as a solvent medium for the reaction, or by heating the compound of general formula V with a solution of sodium hydride and 3-trifluoromethylphenol in dimethylformamide. The reaction is preferably effected at a temperature of from 100° C. to the reflux temperature of the reaction mixture.

The reaction of the compounds of general formula V and the potassium salt of 3-trifluoromethylphenol may be effected by heating a mixture of the compound of general formula V, 3-trifluoromethylphenol and potassium carbonate in a suitable inert aprotic organic solvent, e.g. dimethylformamide or dimethylsulphoxide. The reaction is preferably effected at a temperature of from 100° C. to the reflux temperature of the reaction mixture.

The compounds of general formula V may be prepared by the reaction of 2,4-difluoroaniline, or an acid addition salt thereof, with a compound of the general formula:

(VI)

wherein $Q^1$ represents a group of the general formula:

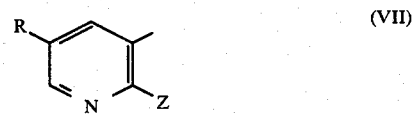
(VII)

(wherein R and Z are as hereinbefore defined) and $T^1$ represents a bromine or, preferably, chlorine atom or a group of the general formula:

(VIII)

wherein W¹ represents a group of general formula VII (wherein R and Z are as hereinbefore defined) or a straight- or branched-chain alkyl group containing from 1 to 4 carbon atoms.

The reaction between 2,4-difluoroaniline or acid addition salts thereof, and the compounds of general formula VI may be effected as hereinbefore described for the reaction of 2,4-difluoroaniline or acid addition salts thereof, with the compounds of general formula II.

The compounds of general formula II, wherein Q and T are as hereinbefore defined may be prepared from compounds of the general formula:

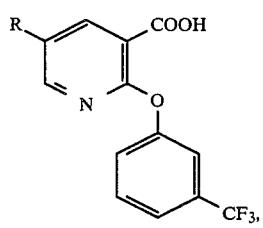
(IX)

wherein R is as hereinbefore defined, by known methods for the preparation of carboxylic acid chlorides, bromides, anhydrides or mixed anhydrides, for example by reaction of a compound of general formula IX with thionyl chloride or bromide, acetic anhydride or an alkyl chloroformate, wherein the alkyl moiety contains from 1 to 4 carbon atoms, e.g. methyl chloroformate or ethyl chloroformate.

The compounds of general formula IX may be prepared according to the procedure described by P. J. Villani et al, J. Med. Chem. 18, 1, (1975), for example by the reaction of 2-chloronicotinic acid with 3-trifluoromethylphenol in the presence of sodium metal and methanol.

The compounds of general formula VI may be prepared from 2-chloronicotinic acids or 2-bromonicotinic acids by application of the procedures hereinbefore described for the preparation of compounds of general formula II from compounds of general formula IX.

The following Examples illustrate the preparation of the compounds of the present invention.

EXAMPLE 2

A mixture of thionyl chloride (465 ml) and 2-(3-trifluoromethylphenoxy)nicotinic acid [930 g; described by F. J. Villani et al, J. Med. Chem. 18, 1 (1975)] was allowed to stand at ambient temperature for 18 hours and was then heated at reflux for 1 hour. Toluene (1 liter) was then added and the solution was evaporated under reduced pressure. The residue thus obtained was dissolved in methylene chloride (3 liters) and treated, with stirring, with triethylamine (453 ml) at ambient temperature. 2,4-Difluoroaniline (422 g) was then added over 1 hour while maintaining the temperature at 10° to 15° C. and the mixture was then heated at reflux for 2 hours. The methylene chloride was removed by distillation and the residue was treated with water (4 liters). A solid of spongy texture was obtained which was filtered off, dried at 50° C. and recrystallised from a mixture of toluene and hexane (2:3; 15 liters), to give N-(2,4-difluorophenyl)-2-(3-trifluoromethylphenoxy)nicotinamide (720 g), m.p. 160°-161° C. as a colourless crystalline solid.

EXAMPLE 3

A mixture of thionyl chloride (1.5 ml) and 5-methyl-2-(3-trifluoromethylphenoxy)nicotinic acid (4 g) was heated at reflux for 15 minutes. Toluene (20 ml) was added and the solution was evaporated under reduced pressure. The residue was dissolved in chloroform (20 ml) and treated, with stirring, with a solution of triethylamine (1.9 ml) and 2,4-difluoroaniline (1.74 g) in chloroform (10 ml) at ambient temperature. The solution was then heated at reflux for 1 hour and cooled. Chloroform (70 ml) was added and the chloroform solution was washed successively with 2N hydrochloric acid (100 ml), aqueous 2N sodium carbonate solution (100 ml) and water (100 ml), dried over magnesium sulphate and evaporated under reduced pressure. The residue thus obtained was recrystallised from a mixture of toluene and hexane (1:1; 50 ml) to give N-(2,4-difluorophenyl)-5-methyl-2-(3-trifluoromethylphenoxy)nicotinamide (3.18 g), m.p. 133°-135° C., as a colourless solid.

5-Methyl-2-(3-trifluoromethylphenoxy)nicotinic acid used as a starting material in the above preparation, was prepared as follows:

2-Bromo-5-methylnicotinic acid [3.45 g; described by J. J. Baldwin et al, J. Org. Chem. 43, 2529 (1978)] was added to a solution of 3-trifluoromethylphenol (7.8 g) and sodium hydride (0.77 g) in methanol (10 ml).

The methanol was removed by distillation and the residue was heated at 130° C. for 18 hours. After cooling, the residue was added to water (100 ml) and the solution thus obtained was extracted with diethyl ether (3×100 ml). The aqueous layer was separated and acidified with concentrated hydrochloric acid to precipitate a pale brown solid. The solid was collected on a filter, washed with water and dissolved in a mixture of methylene chloride and tetrahydrofuran (2:1; 300 ml). The organic mixture thus obtained was dried over magnesium sulphate and evaporated under reduced pressure to give 5-methyl-2-(3-trifluoromethylphenoxy)nicotinic acid (4.3 g), m.p. 173°-175° C., as a colourless crystalline solid.

We claim:

1. A nicotinamide derivative of the general formula:

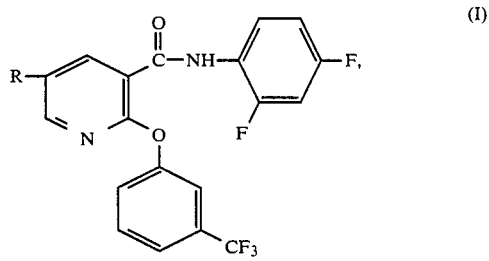
(I)

wherein R represents a hydrogen atom or a methyl group.

2. The nicotinamide derivative according to claim 1 wherein R represents a hydrogen atom.

3. The nicotinamide derivative according to claim 1 wherein R represents a methyl group.

4. A herbicidal composition which comprises, as active ingredient, a herbicidally effective amount of a nicotinamide derivative of general formula I depicted in claim 1, wherein R represents a hydrogen atom or a methyl group in combination with a herbicidally acceptable diluent or carrier.

5. A method for controlling the growth of weeds at a locus which comprises applying a herbicidal composition to the locus pre-emergence of the weeds, which herbicidal composition comprises, as the active ingredient, a herbicidally effective amount of a nicotinamide derivative of the general formula:

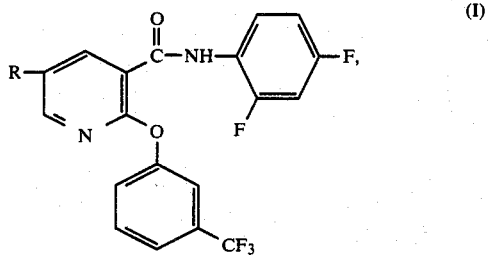

(I)

wherein R represents a hydrogen or a methyl group.

6. A method according to claim 5, in which the weeds are *Aethusa cynapium, Abutilon theophrasti, Amaranthus retroflexus, Amsinckia intermedia, Anagallis arvensis, Anthemis arvensis, Atriplex patula, Brassica nigra, Capsella bursapastoris, Chenopodium album, Chrysanthemum segetum, Cirsium arvense, Datura stramonium, Desmodium tortuosum, Emex australis, Euphorbia helioscopia, Fumaria officinalis, Galeopis tetrahit, Galium aparine, Geranium dissectum, Ipomea purpurea, Lamium purpureum, Lapsana communis, Matricaria inodora, Monochoria vaginalis, Papaver rhoeas, Physalis longifolia, Plantago lanceolata, Polygonum, Portulaca oleracea, Raphanus raphanistrum, Rotala indica, Rumex obtusifolius, Saponaria vaccaria, Scandix pecten-veneris, Senecio vulgaris, Sesbania florida, Sida spinosa, Silene alba, Sinapis arvensis, Solanum nigrum, Sonchus arvensis, Spergula arvensis, Stellaria media, Thlaspi arvense, Tribulus terrestria, Urtica urens, Veronica hederifolia, Veronica persica, Viola arvensis, Xanthium strumarium* or mixtures thereof broad-leafed weeds.

7. A method according to claim 5, in which the weeds are Alopecurus myosuroides, *Apera spica-venti, Agrostis stolonifera, Avena fatua, Avena ludoviciana, Brachiaria, Bromus sterilis, Bromus tectorum, Cenchrus, Cynodon dactylon, Digitaria sanquinalis, Echinochloa crus-galli, Eleusine indicia, Setaria viridis, Sorghum halepense,* or mixtures thereof grass weeds.

8. A method according to claims 5, 6 or 7 in which the herbicidal composition is applied to an area used, or to be used, for growing crops.

9. A method according to claim 8 in which the herbicidal composition is applied to a crop-growing area at a rate sufficient to control the growth of weeds without causing substantial permanent damage to the crop.

10. A method according to claims 5, 6 or 7 which the herbicidal composition is applied at a rate such as to apply the nicotinamide derivative at a rate between 0.01 kg and 10 kg per hectare.

11. A method according to claim 10 wherein the herbicidal composition is applied to an area used, or to be used, for growing a crop of cereals, soyabeans, field or dwarf beans, peas, lucerne, cotton, peanuts or permanent or sown grassland before or after sowing of the crop or before or after energence of the crop.

12. A method according to claim 11 wherein the crop is wheat, barley, maize or rice.

13. A method according to claim 10 wherein the herbicidal composition comprises, as active ingredient, the nicotinamide derivative of general formula I depicted in claim 1 wherein R represents a hydrogen atom and the herbicidal composition is applied to an area used, or to be used, to grow a crop of sunflowers.

14. A method according to claim 8 wherein the herbicidal composition is applied to an area used, or to be used, for growing a crop of cereals, soyabean or cotton before emergence of both the crop and weeds.

15. A method according to claim 14 wherein the crop is wheat, barley, maize or rice.

16. A method according to claim 8 wherein the herbicidal composition comprises, as active ingredient, the nicotinamide derivative of general formula I wherein R represents a hydrogen atom and the herbicidal composition is applied to an area used, or to be used, to grow a crop of sunflowers before emergence of both the crop and weeds.

17. A method according to claim 14, wherein the crop is maize or soyabean and the weeds controlled are selected from the group consisting of *Echinochloa crusgalli, Digitaria sanguinalis* and *Abutilon theophrasti.*

18. A method according to claim 14, wherein the crop is wheat and the weed controlled is *Avena fatua.*

19. A method according to claim 14 wherein the weed controlled is *Ipomoea purpurea.*

20. A method according to claim 11, wherein the herbicidal composition is applied at a rate so as to apply the nicotinamide derivative at a rate of 0.01 kg to 4.0 kg per hectare.

21. A method according to claim 20 wherein the herbicidal composition is applied at a rate so as to apply the nicotinamide derivative at a rate of 0.05 to 2.0 kg per hectare.

* * * * *

UNITED STATES PATENT AND TRADEMARK OFFICE
CERTIFICATE OF CORRECTION

PATENT NO. : 4,618,366
DATED : October 21, 1986
INVENTOR(S) : Michael C. CRAMP et al It is certified that error appears in the above-identified patent and that said Letters Patent is hereby corrected as shown below:

Amend the face of the patent by adding the following:

-- Foreign Application Priority Data

Nov. 3, 1981   Iran .............. 25029 --.

Signed and Sealed this

Seventeenth Day of March, 1987

Attest:

DONALD J. QUIGG

Attesting Officer

Commissioner of Patents and Trademarks